United States Patent [19]
Cornell et al.

[11] Patent Number: 5,741,712
[45] Date of Patent: *Apr. 21, 1998

[54] RECEPTOR MEMBRANES

[75] Inventors: Bruce Andrew Cornell; Vijoleta Lucija Bronislava Braach-Maksvytis, both of New South Wales, Australia

[73] Assignee: Australian Membrane and Biotechnology Research Institute, New South Wales, Australia

[*] Notice: The term of this patent shall not extend beyond the expiration date of Pat. No. 5,436,170.

[21] Appl. No.: 448,178

[22] Filed: May 23, 1995

Related U.S. Application Data

[62] Division of Ser. No. 473,932, Jan. 25, 1990, Pat. No. 5,436,170.

[30] Foreign Application Priority Data

| Jul. 27, 1987 | [AU] | Australia | PI3346 |
| Jul. 27, 1987 | [AU] | Australia | PI3348 |
| Jul. 31, 1987 | [AU] | Australia | PI3453 |
| Sep. 21, 1987 | [AU] | Australia | PI4478 |

[51] Int. Cl.⁶ .......... G01N 33/53; G01N 33/543; G01N 33/563; G01N 33/566
[52] U.S. Cl. .......... 436/501; 435/7.1; 435/817; 436/512; 436/518
[58] Field of Search .......... 204/403, 418; 435/7.1, 317.1, 817; 436/501, 512, 518, 524, 525, 532, 547, 527

[56] References Cited

U.S. PATENT DOCUMENTS

| 4,490,216 | 12/1984 | McConnell . |
| 4,517,303 | 5/1985 | Freytag et al. . |
| 4,661,235 | 4/1987 | Krull et al. . |
| 4,758,342 | 7/1988 | Heckmann et al. . |
| 5,443,955 | 8/1995 | Cornell et al. . |

FOREIGN PATENT DOCUMENTS 87308282  9/1987  European Pat. Off. .

OTHER PUBLICATIONS

Williams, D.E., "Electrochemical Noise" and Chemical Sensing. *Materials Development Division Harwell Laboratory,* (One day conference in Boston, Mass., Nov. 9, 1987), pp. 203–208.

Huang, et al., Interactions of Immunoliposomes with Target Cells, *The Journal of Biological Chemistry,* No. 22, Issue of Nov. 22, pp. 14034–1440, 1983.

*Primary Examiner*—James C. Housel
*Assistant Examiner*—Rodney P. Swartz
*Attorney, Agent, or Firm*—Fish & Richardson, P.C.

[57] ABSTRACT

The present invention provides a biosensor that detects an analyte in a sample by measuring the response of a membrane within which associated ion channels undergo state changes upon interaction between the analyte and the ionic channels. The state change response is detected as result of the change in ionic flow through the membrane.

33 Claims, 4 Drawing Sheets

FIG. 1

CHO

L-Val 1

Gly 2

L-Ala 3

D-Leu 4

L-Ala 5

D-Val 6

L-Val 7

D-Val 8

L-Trp 9

D-Leu 10

L-Trp 11

D-Leu 12

L-Trp 13

D-Leu 14

L-Trp 15

$NHCH_2CH_2OH$

CLOSED

IgG

OPEN

RECEPTOR MEMBRANES

This is a divisional of application Ser. No. 07/473,932, filed Jan. 25, 1990, now U.S. Pat. No. 5,436,170.

The present invention relates to membranes incorporating either receptor molecules and/or ion channels.

It is known that amphiphilic molecules may be caused to aggregate in solution to form two or three dimensional ordered arrays such as monolayers, micelles, black lipid membranes, and vesicles or liposomes, which vesicles may have a single compartment or may be of the multilamellar type having a plurality of compartments. It is also known that such amphiphilic molecules may be formed with cross-linkable moieties. Under appropriate stimulus, such as UV radiation or ionising radiation, the cross-linkable moieties can be caused to polymerize after the amphiphilic molecules have been caused to assume a suitably ordered two or three dimensional array. It is also known that suitable receptor molecules may be included in ordered arrays of amphiphilic molecules.

The selectivity and flux of ions through membranes can depend on the number, size and detailed chemistry of the pores or channels that they possess. It is through these pores or channels that the permeating solute molecules pass across the membrane.

It is known that membranes may incorporate a class of molecules, called ionophores, which facilitate the transport of ions across these membranes. Ion channels are a particular form of ionophore, which as the term implies, are channels through which ions may pass through membranes.

Membranes incorporating ionophores exist in nature, and may also be produced artificially. Australian Patent Application No. 40123/85 discloses the use of membranes including ionophores in biosensors. The ionophore exemplified in this reference is acetylcholine receptor. The acetylcholine receptor functions as a gated ionophore in that it requires the presence of acetylcholine before the acetylcholine receptor is able to facilitate the passage of ions across the membranes. This situation is similar to that encountered at nerve synapses.

The present invention consists in a membrane comprising a closely packed array of self-assembling amphiphilic molecules, the membrane being characterised in that (1) the membrane includes a plurality of ion channels selected from the group consisting of peptides capable of forming helices and aggregates thereof, podands, coronands, cryptands and combinations thereof; and/or (2) at least a proportion of the self-assembling amphiphilic molecules comprise a receptor molecule conjugated with a supporting entity, the receptor molecule having a receptor site, the receptor molecule being selected from the group consisting of imunoglobulins, antibodies, antibody fragments, dyes, enzymes, and lectins; the supporting entity being selected from the group consisting of a lipid head group, a hydrocarbon chain(s), a cross-linkable molecule and a membrane protein; the supporting entity being conjugated with the receptor molecule at an end remote from the receptor site.

The amphiphilic molecules are normally surfactant molecules having a hydrophilic "head" portion and one or more hydrophobic "tails". Surfactants may be any of the known types, i.e. cationic (e.g. quaternary ammonium salts), anionic (e.g. organosulfonate salts), zwitterionic (e.g. phosphatidyl cholines, phosphatidyl ethanolamines), membrane spanning lipid, or non-ionic (e.g. polyether materials). The amphiphilic molecules are preferably such that they can be crossed linked. For this purpose it is necessary to provide the molecules with a cross-linkable moiety such as a vinyl, methacrylate, diacetylene, isocyano or styrene group either in the head group or in the hydrophobic tail. Such groups are preferably connected to the amphiphilic molecule through a spacer group such as is described in Fukuda et al, J. Amer. Chem Soc 1986 108, 2321-2327.

Polymerisation may be performed by any of the known methods for polymerising unsaturated monomers, including heating with or without a free radical initiator, and irradiating with or without a sensitiser or initiator.

In a preferred embodiment of the present invention the amphiphilic molecules, not including a receptor molecule, include or are decorated with at least one moiety cross-linked with at least one corresponding moiety on another of these molecules. In a further preferred embodiment the ion channels and/or receptor molecule covalently linked to a supporting entity also include or are decorated with at least one moiety cross-linked with at least one corresponding moiety on another molecule.

As stated above, the ion channel used in the present invention is selected from the group consisting of peptides capable of forming helices and aggregates thereof, podands, coronands and cryptands. However, it is preferred that the ion channel is a peptide capable of forming a helix or aggregates thereof.

Podands, cryptands and coronands have been described previously in the scientific literature (see, for example, V. F. Kragten et al., J. Chem. Soc. Chem. Commun., 1985, 1275; O.E. Sielcken et al., J. Amer. Chem. Soc., 1987, 109 4261; J. G. Neevel et al., Tetrahedron Letters, 1984, 25, 2263).

Peptides which form α helices generally need to exist as aggregates in the membrane to form ion channels. Typically, the α helical peptides arrange to form aggregates in such a manner that an ion channel is created through the aggregate.

It is preferred that the ion channel is a peptide which forms a β helix. An example of such peptide is the polypeptide gramicidin A. The primary sequence of gramicidin A is shown in FIG. 1. This molecule has been the subject of extensive study (for further information see Cornell B. A., Biomembranes and Bioenergetics (1987), pages 655–676). The ion channel gramicidin A functions as a polar channel which traverses non-polar biological membranes. It is produced either synthetically or extracted from *Bacillus brevis*. In phospholipid bilayers gramicidin A is thought to exist as a helical dimer which substantially partitions into the hydrophobic region of the bilayer.

When it is desired to cross-link the amphiphilic molecules and the gramicidin A, gramicidin A may be modified by replacing one, two, three or four tryptophan groups in the gramicidin A with a polymerizable group, such as styrene. The polymerizable group is attached to the alpha carbon of the 9,11, 13 and/or 15th amino acid residue of the native gramicidin A.

Further examples of molecules which may be used as ion channels in the present invention include gramicidin B, gramicidin C, gramicidin D, gramicidin GT, gramicidin GM, gramicidin GM$^-$, gramicidin GN$^-$, gramicidin A' (Dubos), band three protein, bacteriorhodopsin, mellitin, alamethicin, alamethicin analogues, porin, tyrocidine, and tyrothricin.

Hereafter, the family of gramicidins will be referred to as simply gramicidin.

In the particular case of gramicidin, when the membrane is a monolayer, a monomer of gramicidin A could be used as the ion channel. In the situation where the membrane is a bilayer, a synthetic analogue of dimeric gramicidin A could be used as the ion channel. This synthetic analogue could be provided with suitable cross-linkable moieties. In addition, where the membrane is a bilayer the ion channel may consist of two gramicidin A monomers, in which each monomer is in a different layer. In this situation the gramicidin A monomers are able to diffuse through the layers and when the two monomers come into alignment an ion channel is formed through the bilayer.

While the membranes of the present invention incorporating ion channels may be used as membrane coatings having high conductance, in a number of applications it is necessary for the conductance of the membrane to be responsive to the presence of an analyte. Therefore, in a preferred embodiment of the present invention, the ion channel is gated by a receptor moiety attached to, or associated with, an end of the ion channel, the receptor moiety being such that it normally exists in a first state, but when bound to an analyte exists in a second state, said change of state causing a change in the ability of ions to pass through the ion channel.

The first state of the receptor moiety will normally be a state in which the passage of ions through the ion channel is prevented or hindered. Attachment of the analyte to the receptor will thus cause the receptor to enter the second state wherein ions may pass through the ion channel. In this arrangement an ion channel may be used to detect as little as a single molecule of analyte. The attachment of a single molecule of analyte will cause an ion channel to open and thus cause a leak of ions across the membrane. After a brief time this ion leak may be detected as the signal for the binding of the analyte to the receptor. The measurement of current flow across membranes due to a single ion channel is known and typically yields a current of 4 pA per channel.

As would readily be appreciated by a person skilled in the art the alternative arrangement is when the receptor moiety is in the first state ions are able to pass through the ion channel and when in the second state the passage of ions through the ion channel is prevented or hindered. The receptor moiety may be any chemical entity capable of binding to the desired analyte and capable of changing the ion channel from its first state to its second state upon binding to that analyte. The receptor moiety is any compound or composition capable of recognising another molecule. Natural receptors include antibodies, enzymes, lectins, dyes and the like. For example the receptor for an antigen is an antibody, while the receptor for an antibody is either an anti-antibody or, preferably, the antigen recognised by that particular antibody.

In a preferred embodiment the receptor moiety is attached to the ion channel, and preferably comprises a peptide end sequence on a polypeptide ion channel, which end sequence can bind to an antibody. The antibody binding causes the shape of the end sequence to change thus permitting ions to flow through the ion channel. The receptor moiety may be attached to the ion channel in any suitable way and is not necessarily formed integrally therewith. The receptor may thus be covalently or non-covalently conjugated with the ion channel.

The analyte may be any suitable molecule or group of molecules which will bind to the receptor moiety and cause it to change its position, spatial configuration or change so as to convert the ion channel from the first to the second state. If the receptor is a peptide then the analyte might be an antibody or immunoglobulin, an enzyme or cell surface receptor. If, however, the receptor were the antibody or enzyme then the analyte might be any molecule that binds thereto.

In the embodiment described above, the receptor moiety in its first state, effectively occludes the ion channel. A variation on this method of gating is to provide on the receptor moiety a compound capable of "plugging" the ion channel. In this embodiment binding of the analyte to the receptor moiety effectively pulls the plugging compound out of the ion channel, thereby enabling ions to pass through the channel. Suitable plugging compounds include the receptor itself or smaller molecules e.g. ethylammonium ions, and methylammonium ions which totally block the ion channel, as do divalent ions, such as the calcium cation. In addition guanadinium ions are effective as partial blockers of ion channels, whilst it is suspected that compounds such as phenols, ethanolamines and longer chain versions of ammonium ions may also be useful as plugging compounds.

In general, it is believed that positively charged species with an ionic diameter of 4 to 6 Angstroms attached to a receptor moiety of sufficient flexibility to allow the ion to enter and "plug" the channel may be used.

In a further preferred embodiment the receptor moiety is an antibody, or preferably an antibody fragment including at least one Fab fragment (hereinafter Fab). In this arrangement, in the first state, Fab allows the passage of ions through the channel, and in the second state prevents the said passage of ions;

In a situation where the ion channel is dimeric gramicidin A and the receptor is Fab attached to the ion channel, without wishing to be bound by scientific theory, it is believed that the passage of ions through the channel is blocked upon the binding of the Fab to the analyte (i.e. second state) due to disruption of the dimeric gramicidin A backbone, or to disruption of the portion of the helix of the dimeric gramicidin attached to the Fab.

In the present invention, where at least a proportion of the amphiphilic molecules comprise a receptor molecule conjugated with a supporting entity, the receptor molecule and the entity together form a new amphiphile. This enables the formation of a membrane having a high density of receptor sites. In principle, the density of receptor sites is limited solely by consideration of steric hindrance between the individual receptor molecules.

In a preferred embodiment of the present invention when the receptor molecule is an antibody fragment, the antibody fragment includes at least one Fab fragment. In a further preferred embodiment of the present invention the supporting entity is either a cross-linkable molecule or membrane proteins, and preferably the cross-linkable molecules is bi-functional. In another preferred embodiment of the present invention the antibody fragment consists of two Fab fragments, each Fab recognizing a different antigen. In yet another preferred embodiment the antibody fragment consists solely of the Fab fragment.

In a further preferred embodiment of the present invention where a proportion of the amphiphilic molecules comprise a receptor molecule conjugated with a supporting entity, the membrane may include receptors each reactive with a different molecule or antigenic determinant. For example where the receptor molecules are a mixture of two different Fabs, it is possible for half the receptors to be directed against one antigenic determinant and the other half to a different antigenic determinant.

An imunoglobulin is a Y-shaped molecule composed of four polypeptide chains (two light and two heavy chains) linked by disulphide bonds. The light and heavy polypeptide chains are folded into globular regions called domains. The portion between the $C_{\gamma 1}$ and $C_{\gamma 2}$ domains of the heavy chains, known as the hinge region (Smyth, D. S. and Utsumi, S. (1967) Nature 216, 332) can be cleaved by proteolytic enzymes. Cleavage by the enzyme papain releases the two arms of the Y-shaped molecule, i.e., the Fab fragments, from the remaining $F_c$ stem portion (Zappacosta, S. et al (1968) J. Immunol. 100, 1268). The Fab fragments are purified by ion exchange chromatography (Notkins, A. L. et al (1968) J. Immunol. 100, 314) and affinity chromatography (De La Farge, F. et al (1976) J. Immunol. 123, 247). In another preferred embodiment of the present invention the Fab fragment is linked to the entity selected from the group comprising lipid head group, a hydrocarbon chain(s), bi-functional cross-linker molecules, and membrane proteins, by means of a covalent bond. Such a covalent linkage takes advantage of the various linkage sites available in the Fab proteins. Groups such as the sulfhydryl group of cysteine residues, $\alpha$-amino, $\epsilon$-amino groups of lysine residues, phenolic hydroxyl groups of tyrosine residues and the imidazole groups of histidine residues, are available for conjugation with any of the entities listed above. Once bonded to the latter molecules, a new amphiphile is formed, and the Fab fragments are hence anchored in the membrane and act as highly sensitive and stable detectors of any chosen antigen presented to the membrane surface.

A particularly preferred membrane protein is the polypeptide gramicidin A. This polypeptide commonly exists in membranes as a dimer.

As would be appreciated by persons skilled in the art recombinant DNA technology may be useful for the preparation of membrane protein-receptor conjugates.

In yet another preferred embodiment of the present invention at least a proportion of the amphiphilic molecules consist of the receptor molecules covalently linked to a hydrocarbon(s). Preferably the receptor molecule is an Fab fragment. By changing the number of hydrocarbon chains it is possible to change the phase of the membrane. Some of the membrane phases which may be achievable by varying the number of hydrocarbon chains are the Hexagonal I ($H_I$) phase, where the membrane forms tubes in which the interior is hydrophobic and the exterior polar, and Hexagonal II ($H_{II}$) phase where the membrane forms tubes in which the exterior is hydrophobic and the interior hydrophilic. Other membrane structures which may be formed are lamellae and micelles.

The use of hydrocarbon chains also lends itself to the binding of the membrane to solid surfaces such as ceramics, oxides, hydrogel, silicon, polymers, and transition metals, in the formation of a biosensor. Preferred transition metals include palladium, gold and platinum. This may be achieved by non-covalent attraction, or by covalent reactions. Thus, vinyl groups on a solid substrate could be copolymerised with a vinyl-terminated lipid, a sulphur-terminated lipid could be adhered to a metal (e.g. gold or palladium) substrate, or condensation or addition reactions could be used to anchor the lipid. Modification of the solid substrate, if necessary, can be achieved using any of the known techniques such as silylation of silica surfaces.

As stated previously, the present invention provides a membrane having a high density of receptor sites. This is particularly true where the receptor molecule is an Fab fragment. Using Fab fragments as the receptor molecules it is possible to achieve a membrane in which up to 2% of the amphiphilic molecules include a Fab fragment. Preferably, from about 1% to about 2% of the amphiphilic molecules include a Fab fragment.

The membranes according to the present invention in which at least a portion of the amphiphilic molecules comprise a receptor molecule bound to an entity, are particularly useful in biosensors. These membranes serve as highly selective binding surfaces to which molecular species to be detected will bind. The binding of the molecule to be detected may be registered by any one of a number of known techniques including:

(a) Ellipsometry, (b) Fluoresence polarisation, (c) Internal reflectometry, (d) Light scattering, (e) Surface plasmon resonance, (f) Surface acoustic wave modification, (g) Potentiometric effects i.e. changes in voltage, (h) Amperometric effects i.e. changes current, (i) Thermal effects i.e. a change in temperature or heat flow, (j) Mass or density changes as may be reflected, for example, in the frequency change of a piezolectric device, (k) Measurement of membrane phase change, (l) Radio immunoassay, and (m) Enzyme-linked immunoassay.

In the situation where the membrane includes an ion channel and in which at least a proportion of the self-assembling amphiphilic molecules comprise receptor molecules conjugated with a supporting entity, it is preferred that the ion channel is gramicidin A, and preferably the receptor molecule is an antibody or antibody fragment including at least one Fab fragment.

In a further preferred embodiment of the present invention the ion channel is gated. In this embodiment the membrane includes an ion channel bound to an analyte in close proximity to an amphiphilic molecule comprising a receptor attached to an entity, the receptor being capable of binding to the analyte. In the absence of any free analyte, the analyte bound to the ion channel is attached to the receptor, thereby enabling ions to pass through the ion channel. Upon the addition of free analyte, there is competition for binding to the receptor, and the analyte bound to the ion channel is released from the receptor, thereby blocking the passage of ions through the ion channel.

In an alternative embodiment the membrane includes an ion channel in close proximity to an amphiphilic molecule comprising a receptor molecule conjugated with a supporting entity. When the receptor molecule is not bound to an analyte it at least partially occludes the ion channel thereby preventing or hindering the passage of ions through the ion channel. Binding of the analyte to the receptor moiety causes a change in the receptor moiety which removes the occlusion of the ion channel thereby allowing ions to pass therethrough. In this embodiment it is preferred that the membrane is a bilayer, the ion channel is two gramicidin monomers or a covalently linked dimer and the receptor moiety is a Fab fragment.

In a further preferred embodiment a linker group is provided between the receptor molecule and the entity and/or between the ion channel and receptor moiety. The linker group attached to the head group of the lipid should be of sufficient length to allow reaction of the receptor molecule by reducing steric hindrance that occurs close to the lipid itself. The linker is preferably not hydrophobic so that it can extend toward the aqueous receptor molecule, and should be terminated with a group amenable to attachment of the receptor molecule. For example, the thiol group of a Fab is suited to attachment to linker-bound maleimide groups or to electrophiles such as alkyl halide groups. Similar considerations arise in devising linker groups for attachment of receptor moieties to ionchannels such as gramicidin A.

The membranes of the present invention have particular application in the production of biosensors. Accordingly, a preferred embodiment of the present invention provides a biosensor incorporating the membrane of the present invention.

Methods for measuring the change in conductance of self-assembling membranes, with and without ionophores, are comprehensively described in the scientific literature, and include the use of black lipid membrane chambers, electrodes in which a monolayer, bilayer or bulk lipid is made to coat porous papers, polymers or ceramics and patch clamping in which approximately 1 to 10 ion channels are incorporated in a monolayer or bilayer supported on a microelectrode. The method of signal analysis can be a two, three or four terminal impedance measurement in which the frequency characteristics, noise spectra, cyclic voltammetry or statistics on the inherent making or breaking of ion channels are used to characterise changes in conductance through the membrane.

One of the major difficulties encountered to date in the use of membranes in the formation of biosensors has been the fragility of the membrane. The present inventors have overcome this difficulty and formed he membrane of the present invention on a solid surface and found that this membrane is robust.

This method involves providing on the membrane and the solid surface groups capable of reacting with each other. The preferred solid surfaces include hydrogel, ceramics, oxides, silicon, polymers and transition metals. Preferred transition metals are gold, platinum and palladium. A preferred solid surface in the formation of a biosensor is a palladium-coated glass electrode.

In a preferred embodiment, the present invention provides a biosensor comprising a membrane bilayer attached to a solid surface, the bilayer having an upper and lower layer, the lower layer being adjacent the solid surface and being provided with groups reactive with the solid surface or with groups provided thereon; each layer of the bilayer being composed of self-assembling amphiphilic molecules and gramicidin monomers, and wherein a proportion of the amphiphilic molecules in the upper layer comprise a receptor molecule conjugated with a supporting entity, the receptor molecule having a recptor site, the receptor molecule being selected from the group consisting of immunoglobulins, antibodies, antibody fragments, dyes, enzymes and lectins, and the supporting entity being selected from the group consisting of a lipid head group, a hydrocarbon chain(s), a cross-linkable C molecule, and a membrane protein; the supporting entity being conjugated with the receptor molecule at an end remote from the receptor site.

In this embodiment it is preferred that the receptor molecule is an antibody fragment and preferably is a Fab fragment. It is also preferred that the solid surface is a palladium-coated glass electrode.

In a further embodiment the present invention provides a biosensor comprising a membrane bilayer attached to a solid surface, the bilayer having an upper and lower layer, the lower layer being adjacent to the solid surface and being provided with groups reactive with the solid surface or with groups provided thereon; each layer of the bilayer being composed of self-assembling amphiphilic molecules and gramicidin monomers; and wherein a receptor moiety is attached to the gramicidin monomers in the upper layer.

As would be appreciated by a person skilled in the art, in a biosensor, reducing the area of the membrane will increase the sensitivity and selectivity of the sensor by improving its signal dynamic range and band width.

The present invention will now be described by way of reference to the following figures in which:

FIG. 1 shows the structure of gramicidin A;

Figure 2:
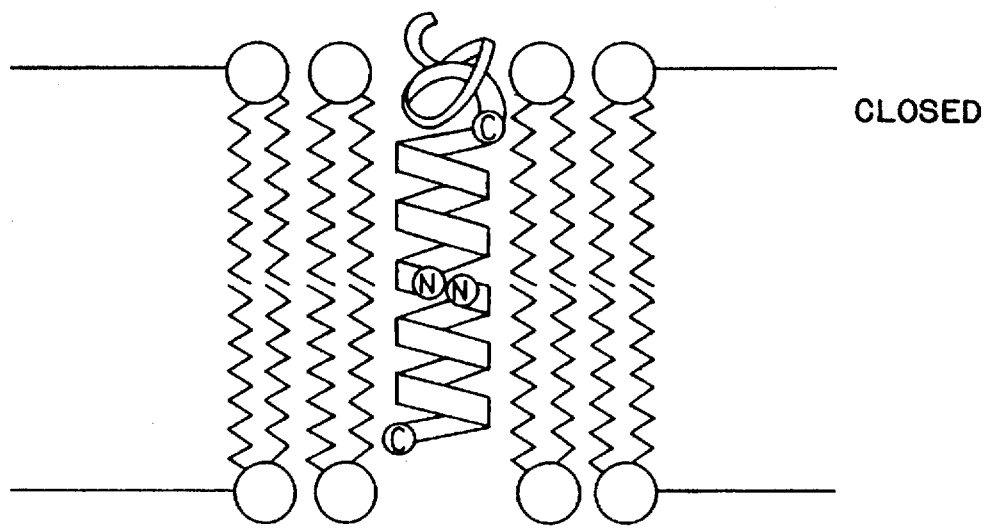
FIG. 2 shows a schematic representation of a gated ion channel.
Figure 2:
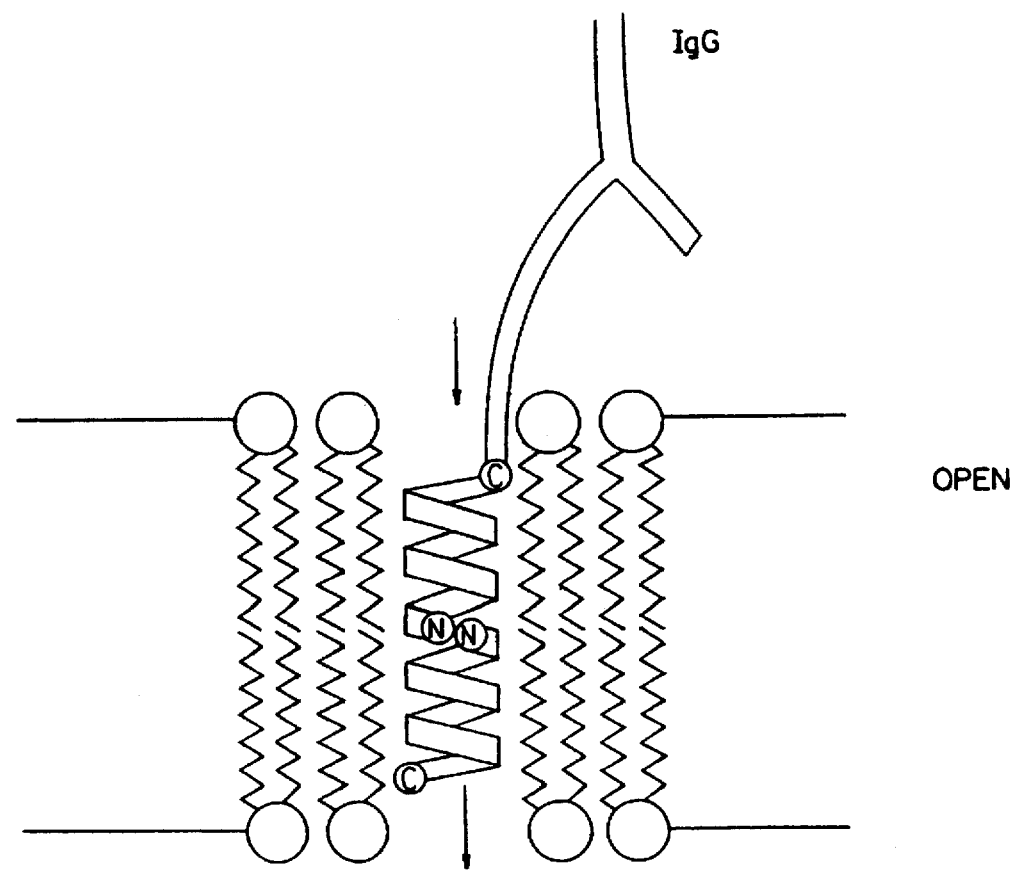
Figure 5:
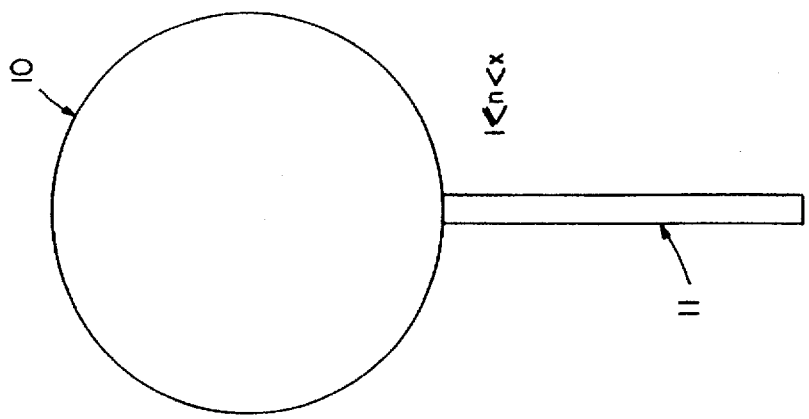
FIGS. 3 to 5 illustrate the manner in which various membrane phases are obtainable.
Figure 4:
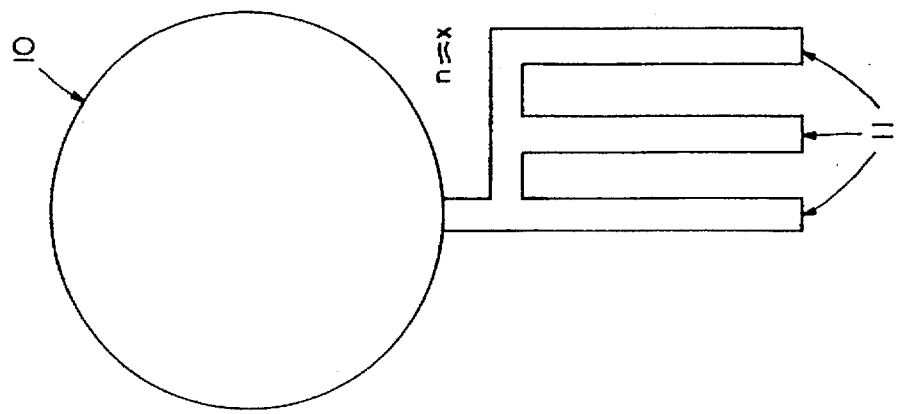
Figure 3:
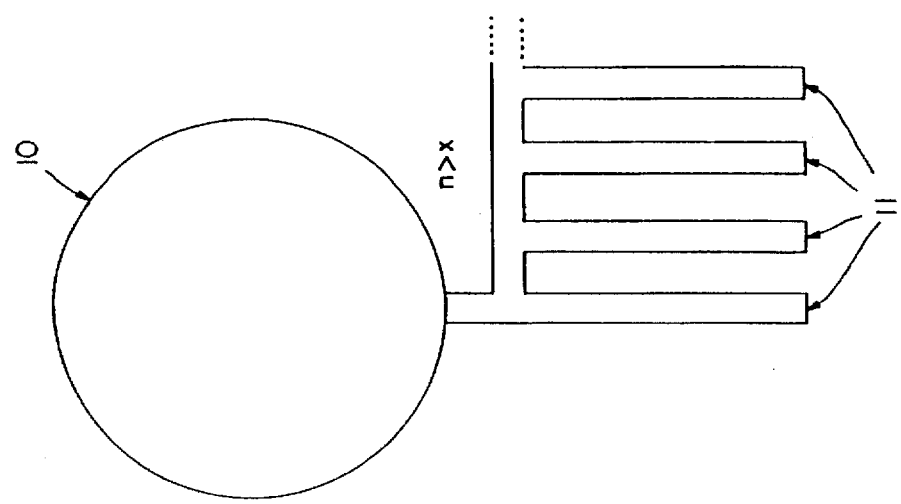
Figure 6:
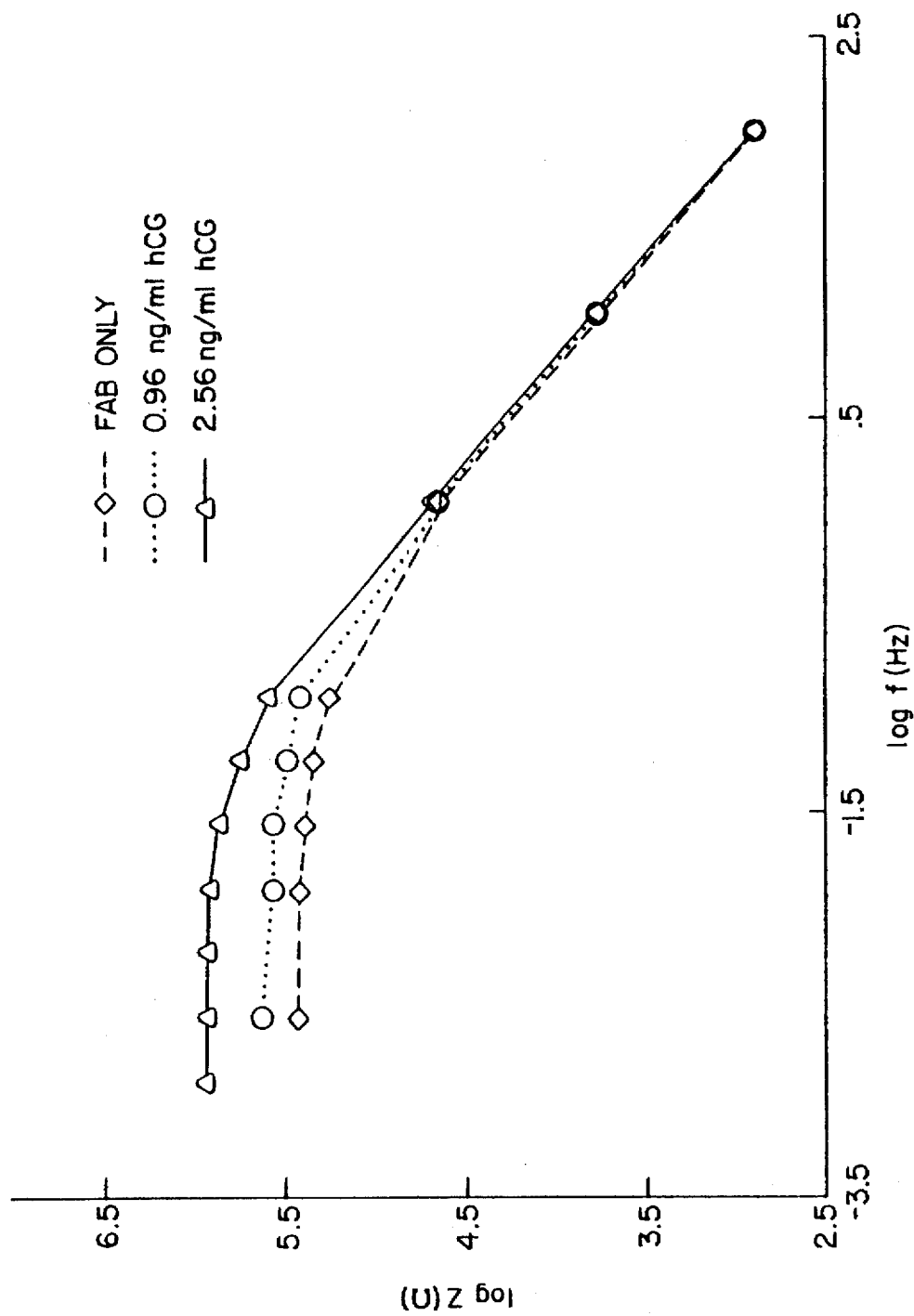
FIG. 6 is a graph showing the detection of an analyte using a membrane biosensor of the present invention formed as per Example 8.

As shown in FIGS. 3 to 5, 10 represents the receptor molecule and 11 represents a hydrocarbon, non-polar moiety of variable length from 8 carbons to 25 carbons containing methylene, alkene, alkyne or substituted aromatic compounds. X represents the number of hydrocarbon groups attached or associated with the receptor moiety 10. This number will depend on the bulk of the polar group. For antibody fragments X typically equals approximately 50 in order to achieve a planar membrane. The schematic geometry then dictates the long range structure formed by the aggregated amphiphiles. As is shown in FIG. 3 when the number of hydrocarbon groups is large a hexagonal phase II membrane is produced. FIG. 4 shows that when the number of hydrocarbon groups is approximately 50 a lamellar phase membrane is produced whilst FIG. 5 shows that when the number of hydrocarbon groups is small a micellar phase membrane is produced.

The present invention will now be described with reference to the following examples:

EXAMPLE 1

SYNTHESIS OF CROSS-LINKABLE MOIETIES (i) Synthesis of p-Hydroxystyrene p-Hydroxyacetophenone was converted to 1-(p-acetoxyphenyl)ethanol and then dehydrated using liquid phase dehydration in the presence of potassium acid sulfate to produce p-acetoxystyrene, according to the method of Corson et al (J. Org. Chem., 1958 23, 544). p-Acetoxystyrene (1.6 g) was added to a stirred solution of potassium hydroxide (1.4 g) in water (14 ml) at 5 degrees Centigrade. Stirring was continued at 0–5 degrees Centigrade for 2h. The mixture was then washed with ether, and the aqueous phase neutralised with saturated sodium hydrogen carbonate solution. The product was extracted into dichloromethane, the solution was dried over anhydrous calcium chloride and the solvent removed, to yield a cloudy oil (0.7 g) which solidified on standing to a waxy solid.

(ii) Synthesis of Methyl 11-(p-Vinylphenoxy)undecanoate

Hydrogen chloride gas was bubbled through a stirred solution of 11-bromoundecanoic acid (2.65 g) in methanol (20 ml) for 1 h at room temperature. The solvent was then removed and the residue in ether was washed with water, dried over anhydrous sodium sulfate and the solvent removed. The residual pale oil (2.8 g, 100%) was identified as methyl 11-bromoundecanoate.

This was converted to 11-(p-vinylphenoxy)undecanoic acid by the method of Hasegawa et al (Polym. Bull. 1985, 14, 31).

(iii) Synthesis of 1-0-(11-p-Vinylphenoxy)undecanoyl)-2-0-octadecylglycerol

The method of Hasegawa et al (Polym. Bull., 1985, 14, 31) was followed, however, the condensation step was allowed to react for 5 days, and the product was chromatographed on silica gel, eluting with ether/light petroleum (1:3). The total product from 0.92 g 11-(p-vinylphenoxy) undecanoic acid was 1.25 g (66%).

EXAMPLE 2

SYNTHESIS OF LINKER GROUP FOR ATTACHMENT TO LIPID OR ION CHANNELS (i) 11-Chloro-3,6,9-trioxaundecan-1-ol 1,8-dichloro-3, 6-dioxaoctane was prepared from triethylene glycol, thionyl chloride and pyridine according to the method of C. J. Pedersen (J. Am Chem. Soc., 1967, 89, 7017), b.p. 121°–122° C./15 mm Hg.

A solution of 1,8-dichloro-3, 6-dioxaoctane (40 g) and potassium hydroxide (11.8 g) in ethylene glycol (100 ml) was stirred at 100° C. for 18 h. The mixture was then cooled, filtered and the residue washed with acetone (2×35 ml). The combined filtrate was then distilled to yield the product as a clear oil (13.5 g, 30%), b.p. 120°–122° C./0.2 mm Hg; I.r. (liquid film) 3430 cm$^{-1}$.

(ii) 11-Chloro-3,6,9-trioxaundec-1-yl succinate

A solution of 11-chloro-3,6,9-trioxaundecan-1-ol (2.00 g), succinic anhydride (0.941 g), pyridine (0.10 ml) and dimethylaminopyridine (0.02 g) in tetrahydrofuran (10 ml) was refluxed for 24 h. The mixture was cooled and the solvent was removed to yield the product, as a clear oil (2.9 g, 100%). I.r.(liquid film): 3000 (b, CO$_2$H), 1730 (C=O) cm$^{-1}$.

EXAMPLE 3

Attachment of Linker Group to Lipid (i) 1-0-(11-(p-Vinylphenoxy)undecanoyl)-2-O-octadecyl-3-O-(11-chloro-3,6,9-trioxaundec-1-yl succinatoyl)glycerol 11-Chloro-3,6,9-trioxaundec-1-yl succinate (0.60 g) was dissolved in thionyl chloride (5 ml) and refluxed for 31 h. Excess thionyl chloride was removed, toluene (5 ml) was added and removed at 0.1 mm Hg to yield the carboxylic acid chloride as a pale yellow oil (0.64 g, 100%). Lr. (liquid film); 1785 (COCl), 1730 (C=O) cm$^{-1}$.

A solution of the carboxylic acid chloride (0.15 g) in tetrahydrofuran (0.5 ml) was added dropwise to a solution of 1-0-(11-(p-vinylphenoxy)undecanoyl)-2-O-octadecylglycerol (0.300 g) and pyridine (0.10 ml) in tetrahydrofuran (5 ml). The mixture was stirred at room temperature for 18 h and then poured onto water (75 ml). The combined chloroform extracts were washed with sulfuric acid (5%, 50 ml) and brine (50 ml), dried (MgSO$_4$) and evaporated. The crude product was chromatographed on silica, using ethyl acetate/light petroleum, 40:60 v/v as eluent, to yield the product as a clear oil, which solidified on standing (0.215 g, 49%). I.r. (liquid film) 1730 (C=O) cm$^{-1}$. Hereafter this compound is referred to as linker lipid.

(ii) 1-0-[11-(p-Vinylphenoxy)undecanoyl]-2-0-octadecyl-3-O-acetoylglycerol

A mixture of 1-0-[11-(p-Vinylphenoxy)undecanoyl]-2-0-octadecylglycerol (0.20 g), redistilled acetic anhydride (3 ml) and pyridine (0.2 ml) was stirred at room temperature for 18 h. Excess acetic anhydride was distilled and the residue was taken up in chloroform (40 ml). The chloroform was washed with sodium hydrogen carbonate solution (5%, 2×50 ml), hydrochloric acid (5%, 50 ml) water (50 ml), dried (MgSO$_4$) and evaporated to yield the product as a colourless oil (0.16 g, 74%) which was homogeneous by t.l.c. IR 1735 cm$^{-1}$ (c=0). Hereafter this compound is referred to acetate lipid.

EXAMPLE 4

Attachment of a Linker Group to Gramicidin A

A mixture of gramicidin (0.0633 g), 11-chloro-3,6,9-trioxaundec-1-yl succinate (0.032 g), dicyclohexyldiimide (0.021 g) and dimethylaminopyridine (0.020 g) in dichloromethane was stirred at room temperature for 24 h. The mixture was then washed with water (4×50 ml), dried (MgSO$_4$) and evaporated. The crude product was purified by preparative layer chromatography using dioxane as eluent to yield the gramicidin analogue (hereafter gramicidin R) as a white solid 0.309 I.R. 1725 (CO$_2$) 1625 (CONH) cm$^{-1}$.

EXAMPLE 5

Preparation, Isolation and Characterisation of Fab Fragments

IgG antibodies were purified from ascites fluid by chromatography on Protein A to a single band on SDS polyacrylamide gel electrophoresis.

Fab$_2$ fragments were prepared from pure antibodies by pepsin digestion (1:100 enzyme: antibody weight ratio) for 30 minutes at pH 4.2 cation-exchange chromatography yielded the pure active Fab$_2$ fragments as established by the single band of 100,000 molecular weight mark on SDS polyacrylamide gel electrophoresis. Electrophoresis under reducing conditions showed a band at 25,000 molecular weight corresponding to the light chain and heavy chains of the two Fab' components of Fab$_2$.

Fab' were obtained from Fab$_2$ by modification of the method of Martin F. J. et al. (Biochemistry, 1981, 20, 4229–38). Fab$_2$ were reduced with 20 mM dithiothreitol at pH 5.5 for 3 hours at room temperature. Dithiothreitol was removed by ultrafiltration using membranes with 30,000 molecular weight cut-off range. Fab' possessed comparable antigen binding activites to Fab$_2$ and gave a single band at the 50,000 and 25,000 molecular weight markers when SDS electrophoresis was carried out with non-reducing and reducing conditions, respectively. Fab' fragments were freshly prepared prior to linking to, the amphiphilic monolayer.

Fab$_2$ were radiolabelled with $^{125}$I to a specific activity of $10^8$ cpm/mg by chloramine T method. $^{125}$I Fab$_2$ were incorporated into the unlabelled Fab$_2$ to a specific activity of $1\times10^4$ cpm per mg unlabelled Fab$_2$ and Fab fragments prepared as described above.

Covalent Attachment of Fab to Lipid and Binding Assay

Pepsin digestion of antibody and subsequent reduction of the resulting Fab$_2$ to Fab' fragments produces a single reactive thiol group at the carboxyl terminus of the Fab'. Coupling of this thiol group to the lipid molecule is achieved via the reaction with a terminal chlorine on polyethylene oxide attached to the polymerisable lipid molecule.

The monolayer of derivatised lipid was formed by spreading lipid in decane solution on an air-water interface in a Langmuir-Blodgett trough. The nylon peg substrate, previously treated to render surface hydrophobic, was dipped through the interface so that the hydrocarbon chains of the lipid interacted with the surface of the substrate.

The surface of the trough was cleaned of lipid before the substrate was quickly withdrawn and transferred to the Fab' solution.

The lipid-coated substrate was immersed into an aqueous solution of Fab' at a concentration of 0.1 to 1.0 mg/ml of phosphate buffered saline buffer, pH 8. The reaction between the specific thiol on the Fab' and the chlorine of the lipid polyethylene oxide linker group was carried out for 3–20 hours at room temperature under N$_2$. $^{125}$I Fab' was used as a marker of the reaction as it was carried out on the lipid coated substrate.

The Fab' linked lipid coated substrate was then transferred to a microtitre well containing $^{125}$I-hCG at a concentration of 1 to 5 mg/ml, ph 7.4. The radioactivity of the entire substrate was measured after a fifteen minute incubation.

Comparison with a conventional immunoassay using the same amount of antibody in microtitre wells showed that the use of lipid-Fab coating yielded at least a 2-fold improvement in sensitivity.

The same treatment was applied to a palladium-coated glass slide substrate, which showed at least a 3-fold increase in sensitivity compared to conventional immunoassay techniques. A coating of at least $10^{11}$ Fab molecules per $cm^2$ was achieved after incubation times longer than 10 hours as calculated from radioactivity measurements of $^{125}$I-Fab.

Use of 2 types monoclonal Fab fragments, which bind DC to two different sides on the human chorionic gonadotrophin (LCG), gave at least a 50% increase in sensitivity compared to using only one Fab.

EXAMPLE 6

SYNTHESIS OF GRAMICIDIN DIMER

A dimer of covalently linked head to head GA molecules having the sequence: HC-Trp-D-Leu-Trp-D-Leu-Trp-D-Leu-Trp-D-Val-Val-D-Val-Ala-D-Leu-Ala-Gly-Val-Gly-Ala-1-$^{13}$C-D-Leu-Ala-D-Val-Val-D-Val-Trp-D-Leu-Trp-D-Leu-Trp-D-Leu-Trp-NHCH$_2$CH$_2$OH has been synthesised.

Chemicals

Side chain protected BOC-Trp(CHO) and all other BOC amino acids were purchased from Peptide Institute Inc. (Japan).

1-$^{13}$C-DL Leucine ($1^{13}$C,99%) was obtained from Cambridge Isotopes Laboratories (Woburn, Massachusetts). tBOC-Trp(CHO) OCH$_2$PAM resin (0.69 mmol/g) was obtained from Applied Biosystems.

Synthesis

BOC-1$^{13}$-D-Leucine was synthesised, according to the procedure of Prasad et al. (Int. J. Peptide Protein Res 19, 1982, 162–171) with minor variations from the starting material of 1$^{13}$C-DL Leucine.

The 1$^{13}$C-D-Leu$_{18}$ dimer was synthesised by the solid phase method, using a 430A peptide synthesiser (Applied Biosystems) for the addition of all amino acids except the 1-$^{13}$ labelled D-Leu which was added manually.

The synthesis started with BOC-Trp(CHO)-OCH$_2$-PAM resin (0.72 g) containing 0.5 mmol of BOC-Trp(CHO) esterified to 1% cross linked polystyrene.

The first 6 cycles were single couplings of BOC amino acid with all remaining cycles being doubly coupled. First couplings were in DMF and recouplings were done with DCM as solvent.

Each amino acid was added with the following steps:
1. Resin washings in DC.
2. Removal of the BOC group using 33% TFA in DCM for et 80 sec., followed by 50% TFA/DCM for 18.5 minutes.
3. 3 DCM washes.
4. Neutralisation with 10% diisopropylethylamine (DIEA) in DMF for 2×1 min.
5. 5 DMF washes.
6. 26 min. coupling cycle in DMF via amino acid re anhydride (2 fold excess of anhydride) using 2 mmol BOC amino acid and dicyclohexylcarbodiimide (DCC).
7. 5 DCM washes.

Recouple cycle:
1. 1 wash in coupling solvent (DCM).
2. 10% DIEA in DCM for 30 sec.
3. 5 DCM washes.
4. Recoupling in DCM 30 minutes.
5. 1 DMF wash.
6. 5 DCM washes.

The 1-$^{13}$C-labelled D-Leu was added to the peptide manually. The resin was removed from the synthesiser of reaction vessel after step 5 (neutralisation and washings) of this cycle.

One equivalent (0.5 mmol) of BOC 1-$^{13}$C-D-Leu was added in 2 ml DCM and stirred for 10 min. One equivalent of DCC in 2 ml of DMF was then added and allowed to react at room temperature overnight.

The resin was then returned to the synthesiser where it was washed and then recoupled with unlabelled BOC-D-Leu using the above recoupling cycle.

Resin samples were taken on completion of each cycle in the synthesis to determine the extent of coupling using quantitative ninhydrin assay (Satin et al. Analytical Biochemistry, 117, 147–157, 1981). Each reaction was 99% complete.

The completed peptide was removed from the resin by reaction with ethanolamine to give the terminal ethanolamide moiety, followed by de-BOCing and formylation reactions as described by Prasad et al. (1982).

Initial purification of the crude peptide was obtained by filtration in methanol on a 100 cm×3.2 cm id column of Sephadex LH20 (Pharmacia).

Fractions collected from this column were analysed by reversed phase HPLC on a radial compression column (8 mm id×10 cm) using either an isocratic aq MeOH solvent (92% MeOH) or a 92% aq MeOH to 100% MeOH gradient.

Analytical TLC's were done on silica gel plates (Merck Kieselgel 60 F-254) using solvents.

Chloroform/MeOH/glacial acetic acid 90:10:3 and CHCl$_3$/MeOH/H$_2$O 65:25:4 and Bands were visualised by ultraviolet light.

The following examples relate to a biosensor fabricated from an amphiphile-ion channel surface attached to a metal electrode. Receptor molecules are covalently linked to the amphiphile-ion channel coating. The binding of the ligand to the receptor molecules act as the gating mechanism, changing the conductance of the ion channel. The gating mechanism is related to ion channel concentration and receptor concentration, as exemplified by the following:

EXAMPLE 7

Synthesis of a Biosensor

A lipid gramicidin surface was prepared on a palladium-coated glass electrode as described in Example 5. The first monolayer consisted of dodecane-thiol:gramicidin (ratio 30 to 1) and the second monolayer consisted of acetate lipid:gramicidin R (at a ratio of 100 to 1). The formation of the gramicidin R was as described in Example 4.

The electrode was then incubated in an Fab solution consisting of Fab prepared from two monoclonal antibodies to hCG which bind to two distinct sites on the hCG molecule. The ratio of the two types of Fab was 1:1. Total concentration of Fab was 0.1 to 1.0 mg/ml of phosphate buffered saline, pH 8. The electrode was incubated at room temperature for 3 to 19 hours. The electrical impedance of the electrode was measured through a frequency range of 1 millihertz to 5 kilohertz, using three electrode system, a "Solartron 1250 FRA" impedance analyser and an electrochemical interface amplifier. Impedance of the lipid gramicidin bilayer was $10^{4.95}$ ohms at 10 millihertz corresponding to $1.6 \times 10^6$ conducting gramicidin channels. (All estimates of number of conducting channel are based on the gramicidin resistance in black lipid membranes of $10^{11}$ ohms/channel.)

Optimal incubation time was twelve hours in the Fab solution, which gave an increased impedance measurement of $10^{6.15}$ ohms at 10 millihertz arising from $5.9 \times 10^4$ conducting gramicidin channels (measured at 1 millihertz). Washing the electrode in running water and leaving in distilled water for 48 hours did not change the impedance of the electrode.

The electrode was incubated with hCG in 0.1 M NaCl for 15 minutes at 37° C. After washing with distilled water, the electrode was returned to the 0.1 M NaCl cell and its impedance was measured. An incubation time of 12 hours in an Fab solution was found to give the most sensitive change in impedance upon hCG binding. 0.96 nanograms hCG per ml gave an increased impedance of $10^{6.20}$ ohms at 10 millihertz corresponding to $4.8 \times 10^4$ conducting gramicidin channels, measured at 1 millihertz.

Washing the electrode with distilled water or ethanol, did not change the impedance. Soaking the electrode in distilled water or 0.1 M NaCl for 24 hours also did not change the impedance of the electrode.

EXAMPLE 8

Palladium-Coating Glass Electrodes were coated using the method described in Example 7. The first monolayer is as described in Example 7, and the second monolayer consisted of total lipid:gramicidin at a ratio of 100:1, where the total lipid consisted of acetate lipid: linker lipid (see Examples 1 to 3) at a ratio of 100:1.

The impedance of the electrode was measured as described in Example 7. The electrode was incubated in Fab solution for 5 to 19 hours as described in Example 7. A lipid-Fab electrode measured after 5.5 hours incubation in the Fab solution gave an impedance of $10^{5.4}$ ohms at 10 millihertz corresponding to $1.9 \times 10^5$ conducting gramicidin channels, compared to a lipid-gramicidin only bilayer impedance of $10^{4.6}$ ohms at 10 millihertz.

hCG was incubated with the Fab covered lipid-gramicidin coated electrode as described in Example 7. The incubation time of 5.5 hours in the Fab solution was found to give the most sensitive change in impedance upon hCG binding. An impedance of $10^{5.55}$ ohms at 10 millihertz corresponding to $1.2 \times 10^5$ conducting gramicidin channels was measured after addition of 0.96 nanograms hCG per ml. A further addition of hCG to a total concentration of 2.56 nanograms per ml increased the impedance in the electrode to $10^{5.93}$ ohms at 10 millihertz corresponding to $5.6 \times 10^5$ conducting gramicidin channels.

Another electrode with the same coating as described above, gave an impedance measurement of $10^{5.8}$ ohms at 10 millihertz with 5.5 hours Fab incubation and an impedance measurement of $10^{6.15}$ ohms at 10 millihertz with addition of 0.96 nanograms hCG per ml. As a control, addition of the same amount of bovine serum albumin instead of hCG (i.e. $1.92 \times 10^{-14}$ mol per ml) gave an impedance measurement of $10^{5.80}$ ohms at 10 millihertz, equivalent to the lipid-Fab coated electrode without hCG.

EXAMPLE 9

Palladium-coated glass electrodes were coated using the method described in Example 7. The first monolayer was dodecanethiol:gramicidin A(10:1) and the second monolayer consisted of acetate lipid:gramicidin linker (2:1). The impedance measurements were carried out as described in Example 7.

The bilayer impedance was $10^{5.95}$ ohms at 1 mHz. Incubation with Fab solution for 16 hours as described in Example 7 gave an impedance of $10^{6.9}$ ohms at 1 mHz. Addition of 0.08 nanograms hCG/ml gave an impedance measurement of $10^{6.56}$ ohms at 1 mHz.

EXAMPLE 10

$Ca^{2+}$ ions specifically block gramicidan channels. $Ca^{2+}$ ions were added to the lipid-gramicidin linker coated electrode to test the ability of $Ca^{2+}$ to block gramicidin.

A palladium-coated glass electrode was prepared by the method described in Example 6 with the first monolayer consisting of dodecanethiol:gramicidin A(10:1) and second monolayer of dimyristoylphosphatidylethanolamine: gramicidin R (1:1). Impedance measurements were made as described in Example 7. The bilayer measured an impedance of $10^{5.05}$ ohms at 10 mHz. Addition of 50 mM $Ca^{2+}$ ions to the measuring cell increased the impedance to $10^{5.35}$ ohms at 10 mHz indicating a decrease in the number of conducting gramicidin channels.

We claim:

1. A biosensor for use in detecting the presence or absence of an analyte in a sample, the biosensor comprising a membrane comprising a closely packed array of selfassembling amphiphilic molecules, the membrane including a plurality of ion channels selected from the group consisting of peptides capable of forming helices and aggregates thereof, podands, cryptands and coronands, a first receptor moiety being attached to the ion channel at an end thereof, the first receptor moiety being such that it normally exists in a first state, said change of state of the first receptor moiety causing a change in the ability of ion flow across the membrane.

2. A biosensor as claimed in claim 1 in which the first receptor moiety is an antibody or antibody binding fragments.

3. A biosensor as claimed in claim 2 in which the ion channels are peptides which form an β helix.

4. A biosensor as claimed in claim 3 in which the ion channels are gramicidin or analogs thereof.

5. A biosensor as claimed in claim 1 in which the amphiphilic molecules and/or the ion channels each include or are decorated with at least one moiety cross-linked with at least one corresponding moiety on another molecule.

6. A biosensor as claimed in claim 1 in which the membrane is attached to a solid surface, the attachment being by means of groups provided on the membrane, said groups being reactive with the solid surface or groups provided hereon.

7. A biosensor as claimed in claim 1 in which the ion channel is dimeric gramicidin A and the first receptor moiety is an antibody or antibody binding fragment, the passage of ions through the ion channel being altered upon the binding of the antibody or antibody binding fragment to an analyte due to the disruption of the dimeric gramicidin A backbone, or to disruption of the portion of the helix of the dimeric gramicidin attached to the antibody or antibody binding fragment.

8. A biosensor as claimed in claim 1 in which the first receptor moiety is a plugging compound which plugs the ion channel or in which a plugging compound which plugs the ion channel is attached to the first receptor moiety, the binding of the analyte to the first receptor moiety causing a change in the relationship between the plugging compound and the ion channel and altering the ability of ions to pass through the ion channel.

9. A biosensor as claimed in claim 7 in which the membrane is attached to a solid surface.

10. A biosensor as claimed in claim 8 in which the membrane is attached to a solid surface.

11. A biosensor as claimed in claim 8 in which the plugging compound is a positively charged species with an ionic diameter of in the range of about 4 to 6 Angstroms.

12. A biosensor as claimed in claim 1 in which the membrane is a bilayer.

13. A biosensor as claimed in claim 1 in which the membrane is a monolayer.

14. A biosensor as claimed in claim 1 in which a proportion of selfassembling amphiphilic molecules are membrane spanning lipids.

15. A biosensor as claimed in claim 1 in which the first receptor moiety is an antigen reactive with an antibody analyte.

16. A biosensor as claimed in claim 1 in which the first receptor moiety is attached to the ion channel via a non-hydrophobic linker group.

17. A biosensor as claimed in claim 4 in which the gramicidin to which the first receptor moiety is attached can diffuse through the membrane.

18. A biosensor as claimed in claim 1 in which at least a proportion of the set-assembling amphiphilic molecules comprise a second receptor moiety conjugated with a supporting entity, the second receptor moiety having a receptor site, the supporting entity being selected from the group consisting of a lipid head group, hydrocarbon chain(s), cross-linkable molecules and a membrane protein, the supporting entity being conjugated with the second receptor moiety at a location remote from the receptor site.

19. A biosensor as claimed in claim 18 in which the second receptor moiety is an antibody or antibody binding fragments.

20. A biosensor as claimed in claim 18 in which the first second receptor moieties are Fab fragments which recognize different antigenic determinants.

21. A biosensor as claimed in claim 18 in which the ion channel are peptides which form an β helix.

22. A biosensor as claimed in claim 21 in which the ion channels are gramicidin or analogs thereat.

23. A biosensor as claimed in claim 18 in which the amphiphilic molecules and/or the ion channels each include or are decorated with at least one moiety cross-linked with at least one corresponding moiety on another molecule.

24. A biosensor as claimed in claim 18 in which the membrane is attached to a solid surface, the attachment being by means of groups provided on the membrane, said group being reactive with the solid surface or groups provided thereon.

25. A biosensor as claimed in claim 18 in which the membrane is a bilayer.

26. A biosensor as claimed in claim 18 in which the membrane is a monolayer.

27. A biosensor as claimed in claim 18 in which a proportion of the self assembling amphiphilic molecules are membrane spanning lipids.

28. A biosensor as claimed in claim 18 in which the second receceptor moiety is an antigen reactive with an antibody analyte.

29. A biosensor as claimed in claim 18 in which the first receptor moiety is attached to the ion channel via a non-hydrophobic linker group.

30. A biosensor as claimed in claim 18 in which the second receptor moiety is attached to the supporting entity via a non-hydrophobic linker group.

31. A biosensor as claimed in claim 22 in which the gramicidin to which the receptor moiety is attached can diffuse through the membrane.

32. The biosensor of claim 1, wherein the first receptor moiety is selected from the group consisting of antigens, immunoglobulins, peptides, antibody binding fragments, enzymes, lectin and dyes.

33. The biosensor of claim 18, wherein the first receptor moiety is selected from the group consisting of antigens, immunoglobulins, peptides, antibody binding fragments, enzymes, lectin, and dyes.

* * * * *